US008586191B2

(12) United States Patent
Lorentz et al.

(10) Patent No.: US 8,586,191 B2
(45) Date of Patent: Nov. 19, 2013

(54) ARTICLE ADHESIVE TO THE SKIN

(75) Inventors: Gilles Lorentz, Lyons (FR); Francois Martin, Luebeck (DE)

(73) Assignee: Bluestar Silicones France, Lyons (FR)

( * ) Notice: Subject to any disclaimer, the term of this patent is extended or adjusted under 35 U.S.C. 154(b) by 0 days.

(21) Appl. No.: 13/576,250

(22) PCT Filed: Jan. 28, 2011

(86) PCT No.: PCT/FR2011/000056
§ 371 (c)(1),
(2), (4) Date: Oct. 16, 2012

(87) PCT Pub. No.: WO2011/092404
PCT Pub. Date: Aug. 4, 2011

(65) Prior Publication Data
US 2013/0053749 A1    Feb. 28, 2013

(30) Foreign Application Priority Data

Feb. 1, 2010   (FR) ..................... 10 00388

(51) Int. Cl.
*B32B 9/04*      (2006.01)
*B32B 27/28*    (2006.01)
(52) U.S. Cl.
USPC ........... 428/447; 156/329; 428/343; 428/353; 428/355 R; 525/478; 602/54

(58) Field of Classification Search
None
See application file for complete search history.

(56) References Cited

U.S. PATENT DOCUMENTS

| 5,534,609 | A | * | 7/1996 | Lewis et al. ..................... 528/15 |
| 5,635,201 | A | * | 6/1997 | Fabo .............................. 424/443 |
| 5,948,515 | A | * | 9/1999 | Tsunekawa .................... 428/215 |
| 7,858,197 | B2 | * | 12/2010 | Ahn et al. ...................... 428/447 |
| 2005/0042462 | A1 | * | 2/2005 | Fehn et al. .................... 428/447 |
| 2007/0042108 | A1 | | 2/2007 | Gantner et al. |
| 2010/0168633 | A1 | * | 7/2010 | Bougherara et al. .......... 602/43 |

FOREIGN PATENT DOCUMENTS

| WO | WO 2005/051442 | * | 6/2005 |
| WO | 2006/028612 A1 | | 3/2006 |

OTHER PUBLICATIONS

International Search Report for PCT/FR2011/000056 Mailed Apr. 21, 2011.

* cited by examiner

*Primary Examiner* — Marc Zimmer
(74) *Attorney, Agent, or Firm* — Miles & Stockbridge P.C.

(57) ABSTRACT

The field of the invention is that of articles adhesive to the skin for medical or paramedical use. The invention relates to an article adhesive to the skin.

6 Claims, No Drawings

ARTICLE ADHESIVE TO THE SKIN

CROSS REFERENCE TO RELATED APPLICATIONS

This application is a §371 National Stage Application of PCT/EP2011/000056, filed Jan. 28, 2011, which claims priority to French Application No. 1000388, filed Feb. 1, 2010.

BACKGROUND OF THE INVENTION

1. Field of the Invention

The field of the invention is that of skin-adhesive articles for medical or paramedical use.

2. Description of Related Art

It is very difficult to adhere materials to low-surface-energy plastics films such as films made of polyester or polyurethane. Copiously described in the prior art are adhesion primers for silicone gels to low-surface-energy plastics films. Typically, the methylhydrogensiloxane polymer solutions produce satisfactory adhesion of the silicone gels to the polyurethane films for cushions and mattresses for preventing bedsores or for external mammary prostheses. In these applications, the silicone gel is completely integrated in a polyurethane film pouch in such a way that no contact is possible between the gel and the exterior.

When, by contrast, tacky silicone gels are used as adhesives for producing, for example, adhesive strips for dressings, the devices for attaching stoma bags, or in certain apparel applications, the methylhydrogensiloxane polymer solutions produce satisfactory adhesion of the silicone gels to the polyurethane films, but the tack of the gels is lost or greatly reduced, such that the adhesive strip no longer exhibits the required performance, this being a problem which may rule it out for this type of application.

SUMMARY

With this being the state of knowledge, one of the essential objectives of the present invention is to provide a skin-adhesive article which no longer exhibits the problems described above.

This objective is achieved by the invention, which relates to a skin-adhesive article comprising:

(1) a plastics substrate S that is preferably a plastics film, coated on at least one of the two faces with:
(2) at least one adhesion primer layer C prepared by:
a) applying a composition composed of:
  i) at least one cyclosiloxane A, and
  ii) at least one crosslinker which is either a polyorganosiloxane oil B comprising at least one alkenyl group bonded to a silicon atom and at least one hydrogen atom bonded to a silicon atom, or a polyorganosiloxane resin F comprising at least one siloxyl unit comprising at least one hydrogen atom bonded to a silicon atom,
b) and drying said adhesion primer layer C by evaporating the cyclosiloxane A, and
(3) at least one layer D applied to the adhesion primer layer C, said layer D consisting of a silicone gel E.

DETAILED DESCRIPTION OF A PREFERRED EMBODIMENT

The Applicant Company has deployed substantial research means and numerous experiments in order to attain this objective among others. And, in terms of this objective, the Applicant has been able to find, quite surprisingly and unexpectedly, that using in the adhesion primer layer, in place of the conventional crosslinkers—such as methylhydrogensiloxane polymers—the polyorganosiloxane oil B or the polyorganosiloxane resin F according to the invention, the resulting adhesion of the silicone gels to the low-surface-energy plastics substrate films is satisfactory, while the tack of the gels is retained or enhanced, such that the article exhibits an excellent functional performance.

The polyorganosiloxane resin F is preferably a resin selected from the group consisting of the following: a resin M'Q in which the hydrogen atoms bonded to the silicon are included in part of the siloxyl units (M), a resin MD'Q in which the hydrogen atoms bonded to the silicon are included in the siloxyl units (D), a resin MM'Q in which the hydrogen atoms bonded to the silicon are included in part of the siloxyl units (M), a resin MM'DQ in which the hydrogen atoms bonded to the silicon are included in part of the siloxyl units (M), and a resin MDT' in which the hydrogen atoms bonded to the silicon are included in the siloxyl units (T), where M, M', D, D', T'', and Q are siloxyl units of formulae below:

$M' = (H)(R_2) SiO_{1/2}$
$M = R_3 SiO_{1/2}$
$D = R_2 SiO_{2/2}$
$D' = (H)(R) SiO_{2/2}$
$T' = (H) SiO_{3/2}$
$Q = SiO_{4/2}$ where the identical or different radicals R represent $C_1$-$C_{18}$ cycloalkyl or alkyl groups.

According to one preferred embodiment, the formula of the polyorganosiloxane oil B is as follows:

$$MD_x D'_y D^{Alk}_z M$$

where:
a) $M = (R^1)_3 SiO_{1/2}$
in which formula the identical or different radicals $R^1$ correspond either to an aryl group or to a linear or branched $C_1$-$C_6$ alkyl group,
b) $D' = (R^2)(H) SiO_{2/2}$
in which formula the radical $R^2$ corresponds either to an aryl group or to a linear or branched $C_1$-$C_6$ alkyl group,
c) $D = (R^3)_2 SiO_{2/2}$
in which formula the radicals $R^3$ have the same definition as $R^2$ described above,
d) $D^{Alk} = (R^4)(X) SiO_{2/2}$
in which formula the radical $R^4$ has the same definition as $R^2$ described above, and the radical X corresponds to an alkenyl group having from 2 to 6 carbon atoms, and preferably a vinyl group,
e) x is between 0 and 200, preferably between 1 and 100, and more preferably between 10 and 50,
f) y is between 1 and 200, preferably between 10 and 100, and more preferably between 40 and 80, and
g) z is between 1 and 50, preferably between 2 and 20, and more preferably between 2 and 10.

According to another embodiment, the substrate is a plastics film made of polyurethane or of polyester.

The silicone gel E is preferably prepared by crosslinking a silicone composition K comprising:
at least one polyorganosiloxane G having on average two alkenyl groups bonded to silicon per molecule, said alkenyl groups each containing 2 to 6 carbon atoms, and no silicon atom being bonded to more than one single alkenyl group,
at least one hydrogen-bearing silicon compound H having at least two and preferably at least three hydrogen atoms bonded to silicon per molecule, optionally at least one nonfunctionalized poly-organosiloxane I, and a platinum-based hydrosilylation catalyst J.

Silicone gels and other gels are commonly used in the medical field, whether for external use (mammary prostheses or medical cushions or mattresses) or for internal use (implanted mammary prostheses). They have a very great mobility and have very good mechanical properties, their density being close to that of human tissue.

For all of these applications, the physical properties of these gels are adapted to the use by varying the levels of siloxyl units bearing vinyl and SiH functions.

In general, the polyorganosiloxane G contains on average two alkenyl groups bonded to silicon per molecule, each alkenyl group being bonded to a different silicon atom. The polyorganosiloxane G is a substantially linear polymer, although a small degree of branching may exist. The alkenyl groups are preferably attached to silicon atoms which are distant from one another in the molecule, and at best they are attached to the terminal silicon atoms of the siloxane chain. The alkenyl groups contain not more than 6 carbon atoms and may be, for example, vinyl, allyl or hexenyl groups, although they are preferably vinyl groups. The remaining organic substituents of the polyorganosiloxane G are selected from alkyl and aryl groups, and are preferably alkyl groups having not more than 8 carbon atoms, and phenyl groups. Examples of these remaining substituents are methyl, ethyl, propyl, isobutyl, and phenyl groups. The compounds most readily employed are α,ω-(dimethylvinylsiloxy) polydimethylsiloxanes or polyorganosiloxanes of poly(dimethylsiloxy) (methylvinylsiloxy) α,ω-(dimethylvinylsiloxy) type.

The polyorganosiloxane G is a commercial product, such as, for example, the products of the Rhodorsil® 621V range from the company Bluestar Silicones, and are widely disclosed in the technical literature with regard both to their structures and to their syntheses.

The polyorganosiloxane G is preferably substantially linear and possesses a dynamic viscosity of less than or equal to 200 000 mPas, preferably to 170 000 mPa·s, and more preferably still between 20 and 165 000 mPa·s.

According to another variant, the % by weight of reactive alkenyl groups bonded directly to a silicon atom is between 0.025% and 3%.

The hydrogen-containing silicon compound H is generally a polyorganosiloxane, or a silane, containing at least 2, preferably 3, hydrogen atoms bonded to silicon per molecule. These hydrogen atoms may be located on terminal siloxane units and also on siloxane units which are in the polymer chain, or else they may be situated solely within the siloxane chain.

In practice, the polyorganohydrogenosiloxanes H employed are, for example, polyorganosiloxanes of poly(dimethylsiloxy) (siloxymethylhydrogeno)-α,ω-(dimethylhydrogenosiloxy) type and α,ω-(dimethylhydrogenosiloxy) polydimethylsiloxanes. These POSs (I) are commercial products and are widely disclosed in the technical literature with regard both to their structures and to their syntheses.

For the nonfunctionalized polyorganosiloxanes I, those most readily employed are α,ω-(trimethylsiloxy) polydimethylsiloxanes or PDMS. These polyorganosiloxanes are commercial products such as, for example, the products of the Rhodorsil® 47V range (for example, 47V50, 47V100, 47V500, 47V12500 or 47V30000) from the company Bluestar Silicones, and they are widely disclosed in the technical literature with regard both to their structures and to their syntheses.

The nonfunctionalized polyorganosiloxanes I are preferably substantially linear and possess a dynamic viscosity of less than or equal to 50 000 mPa·s, preferably between 20 and 40 000 mPa·s.

The catalyst J is another important component of the composition for forming the gel. It is preferably an organometallic platinum complex or else one of the platinum-based catalysts traditionally employed for the catalysis of this type of reactions of, for example, ≡SiH groups and ≡Si-vinyl groups. Examples include platinum black, chloroplatinic acid, an alcohol-modified chloroplatinic acid, a complex of chloroplatinic acid with an olefin, an aldehyde, a vinylsiloxane or an acetylene alcohol, among others. U.S. Pat. No. 2,823,218 discloses a chloroplatinic acid-type hydrosilylation catalyst, and U.S. Pat. No. 3,419,593 relates to catalysts formed by complexes of chloroplatinic acid and vinylsiloxane-type organosilicone. Complexes of platinum and hydrocarbons that are useful as a hydrosilylation catalyst are disclosed by U.S. Pat. Nos. 3,159,601 and 3,159,662. U.S. Pat. No. 3,723, 497 describes a platinum acetylacetonate, and U.S. Pat. No. 3,220,972 relates to catalysts based on platinum alcoholate.

For component J, an effective amount of at least one hydrosilylation reaction catalyst means the amount which is sufficient to initiate the hydrosilylation reaction. As regards the catalytically effective amount to be employed, it is self-evident that the skilled person in the art under consideration is entirely capable of determining the optimum amount of catalyst for promoting the hydrosilylation reaction. This amount depends in particular on the nature of the catalyst and on the POSs under consideration. To give an idea, it may be indicated that the amount will be between 0.001% and 0.5% by weight, relative to the total weight of the composition.

The amount of the constituents G, H, I, and J is preferably selected such that the molar ratio r of the hydrogen atoms bonded to the silicon to the alkenyl radicals (X) bonded to the silicon is between 0.5:1 and 5:1.

The silicone composition K may further comprise at least one addition reaction retardant or a crosslinking inhibitor selected from the following compounds:

polyorganosiloxanes substituted by at least one alkenyl that may optionally be in cyclic form, particular preference being given to tetramethylvinyltetrasiloxane, pyridine, phosphines and organic phosphites, unsaturated amides, alkyl maleates, and acetylenic alcohols.

These acetylenic alcohols (see FR-A-1 528 464 and FR-A-2 372 874), which form part of the preferred thermal blockers of the hydrosilylation reaction, have the following formula:

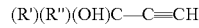

(R')(R")(OH)C—C≡CH in which formula

R' is a linear or branched alkyl radical, or a phenyl radical;

R" is H or a linear or branched alkyl radical, or a phenyl radical; it is possible for the radicals R' and R" and the carbon atom located α to the triple bond to form a ring; and the total number of carbon atoms contained in R' and R" is at least 5, preferably from 9 to 20.

Said alcohols are preferably selected from those having a boiling point of greater than 250° C. Examples include the following:

1-ethynylcyclohexan-1-ol;

3-methyldodec-1-yn-3-ol;

3,7,11-trimethyldodec-1-yn-3-ol;

1,1-diphenylprop-2-yn-1-ol;
3-ethyl-6-ethyl-non-1-yn-3-ol;
2-methylbut-3-yn-2-ol;
3-methylpentadec-1-yn-3-ol.

These α-acetylenic alcohols are commercial products. A retardant of this kind is present at not more than 3000 ppm, preferably at from 100 to 1000 ppm, relative to the total weight of the polyorganosiloxanes in the silicone composition.

Another subject of the invention relates to a dressing or patch for medical or paramedical use, comprising the skin-adhesive article according to the invention and as described above.

With regard to the preparation of the gel, it may be specified that the crosslinking of the composition to a gel takes place at ambient temperature or after heating to temperatures of between 50 and 200° C., for example. In this context, the crosslinking times required are, for example, between a few minutes and 1 hour 30 minutes. These products are widely distributed and described in the trade, and are well known to the skilled person.

The nonlimitative examples which follow show various possibilities for formulation of the compositions according to the invention, and also the characteristics and properties of the silicone gels obtained by crosslinking said compositions.

EXAMPLES

Preparation of the Adhesion Primer of the Invention

The table below describes the inventive formulations of adhesion primers for silicone gels on plastics films. They are composed of 90% by weight of the cyclosiloxane A and 10% by weight of the crosslinker.

|  | Nature of cyclosiloxane (A) | Crosslinker |
|---|---|---|
| Primer A, inventive | Decamethylcyclopentasiloxane | Polyorganosiloxane oil (B) containing Si-vinyl units and Si—H units Silbione 20038 ® sold by Bluestar Silicones |
| Primer B, inventive | Decamethylcyclopentasiloxane | M'Q resin (F) containing Si—H units Resin 10339 ® sold by Bluestar Silicones |
| Primer C, comparative PS 810 E | Decamethylcyclopentasiloxane | Polyorganosiloxane oil containing SiH units (methylhydrogensiloxane polymer) |

Procedure:

2 grams of the crosslinker are diluted in 18 g of decamethylcyclopentasiloxane. The mixture is stirred at ambient temperature for 5 minutes. The plastics substrate is a polyester film with a thickness of approximately 70 μm. The primer is applied to the film with a brush, forming an adhesion primer layer of approximately 40 to 50 g/cm², and then dried at 60° C. for 30 minutes.

RT Gel 4320®, sold by Bluestar Silicones, is subsequently applied with a knife to the adhesion primer layer, and the assembly is dried in an oven at 120° C. for 15 minutes.

Tests Performed

Two parameters were measured on the resulting samples.
the adhesion of the silicone gel to the polyester film, measured by a peeling test of the silicone gel with the finger (rubbing test).
the tack of the silicone gel, using the Probe Tack Device (PT-1000). A tack of 4 mJ/cm² is considered satisfactory for the application.

The results obtained are shown in the table below:

| Sample | Adhesion of the silicone gel to the plastics substrate | Probe tack (mJ/cm²) |
|---|---|---|
| Plastics substrate with inventive primer A | Very good | 6.11 |
| Plastics substrate with inventive primer B | Very good | 4.04 |
| Plastics substrate with comparative primer C | Very good | 0.42 |

These results show that the primers according to the invention allow a good level of tack to be maintained for the gels, while producing excellent adhesion of the silicone gel to the polyester film.

The invention claimed is:

1. A skin-adhesive article comprising:
   (1) a plastics substrate S optionally a plastics film, coated on at least one with:
   (2) at least one adhesion primer layer C prepared by:
      a) applying a composition composed of:
         i) at least one cyclosiloxane A, and
         ii) at least one crosslinker which is either a polyorganosiloxane oil B comprising at least one alkenyl group bonded to a silicon atom and at least one hydrogen atom bonded to a silicon atom, or a polyorgano-siloxane resin F comprising at least one siloxyl unit comprising at least one hydrogen atom bonded to a silicon atom,
      b) and drying said adhesion primer layer C by evaporating the cyclosiloxane A, and
   (3) at least one layer D applied to the adhesion primer layer C, said layer D comprising a silicone gel E.

2. The article as claimed in claim 1, wherein said polyorganosiloxane resin F is a resin selected from the group consisting of the following: a resin M'Q in which the hydrogen atoms bonded to the silicon are included in part of the siloxyl units (M), a resin MD'Q in which the hydrogen atoms bonded to the silicon are included in the siloxyl units (D), a resin MM'Q in which the hydrogen atoms bonded to the silicon are included in part of the siloxyl units (M), a resin MM'DQ in which the hydrogen atoms bonded to the silicon are included in part of the siloxyl units (M), and a resin MDT' in which the hydrogen atoms bonded to the silicon are included in the siloxyl units (T), where M, M', D, D', T', and Q are siloxyl units of formulae below:

$M'=(H)(R_2)SiO_{1/2}$
$M=R_3SiO_{1/2}$
$D=R_2SiO_{2/2}$
$D'=(H)(R)SiO_{2/2}$
$T'=(H)SiO_{3/2}$
$Q=SiO_{4/2}$ where the identical or different radicals R represent $C_1$-$C_{18}$ cycloalkyl or alkyl groups.

3. The article as claimed in claim 1, wherein the formula of said polyorganosiloxane oil B is as follows:

$$MD_xD'_yD^{Alk}_zM$$

where:
a) $M=(R^1)_3SiO_{1/2}$ in which formula the identical or different radicals $R^1$ correspond either to an aryl group or to a linear or branched $C_1$-$C_6$ alkyl group, b) $D'=(R^2)(H)SiO_{2/2}$ in which formula the radical $R^2$ corresponds either to an aryl group or to a linear or branched $C_1$-$C_6$ alkyl group, c) $D=(R^3)_2SiO_{2/2}$ in which formula the radicals $R^3$ have the same definition as $R^2$ described above, d) $D^{Alk}=(R^4)(x)SiO_{2/2}$ in which formula the radical $R^4$ has the same definition as $R^2$ described above, and the radical X corresponds to an alkenyl group having from 2 to 6 carbon atoms, and optionally a vinyl group, e) x is from 0 to 200, optionally from 1 to 100, f) y is from 1 to 200, optionally from 10 to 100, and g) z is from 1 to 50, optionally from 2 to 20.

4. The article as claimed in claim 1, wherein said substrate is a plastics film comprising polyurethane and/or polyester.

5. The article as claimed in claim 1, wherein said silicone gel E is prepared by crosslinking a silicone composition comprising:

at least one polyorganosiloxane G having on average two alkenyl groups bonded to silicon per molecule, said alkenyl groups each containing 2 to 6 carbon atoms, and no silicon atom being bonded to more than one single alkenyl group, at least one hydrogen-bearing silicon compound H having at least two and optionally at least three hydrogen atoms bonded to silicon per molecule, optionally at least one nonfunctionalized polyorganosiloxane I, and a platinum-based hydrosilylation catalyst J.

6. A dressing or patch for medical or paramedical use, comprising the skin-adhesive article as described in claim 1.

\* \* \* \* \*